United States Patent [19]
Ibe

[11] Patent Number: 5,201,229
[45] Date of Patent: Apr. 13, 1993

[54] SENSOR FOR CONTROLLING WATER QUALITY OF REACTOR AND METHOD OF CONTROLLING SAID WATER CHEMISTRY

[75] Inventor: Hidefumi Ibe, Katsuta, Japan
[73] Assignee: Hitachi, Ltd., Tokyo, Japan
[21] Appl. No.: 603,328
[22] Filed: Oct. 25, 1990

[30] Foreign Application Priority Data

Nov. 1, 1989 [JP] Japan .................... 1-283009

[51] Int. Cl.$^5$ .............................. G01N 19/08
[52] U.S. Cl. ............................ 73/799; 73/776
[58] Field of Search ............... 73/799, 802, 775, 776

[56] References Cited

U.S. PATENT DOCUMENTS

| 3,596,269 | 7/1971 | Laska | 73/799 X |
| 4,255,974 | 3/1981 | Dufrane et al. | 73/799 X |

FOREIGN PATENT DOCUMENTS

| 635394 | 11/1978 | U.S.S.R. | 73/799 |
| 9010190 | 9/1990 | World Int. Prop. O. | 73/799 |

Primary Examiner—Hezron E. Williams
Assistant Examiner—Joseph W. Roskos
Attorney, Agent, or Firm—Antonelli, Terry, Stout & Kraus

[57] ABSTRACT

An element (e.g., a sensor) has a fine-line thin film of a conductor formed on a non-conductive substrate, and a change of physical properties (e.g., deformation) of the substrate or the ambient environment is detected through a change in physical properties of the conductor. The element is manufactured by forming a layered film, composed of a semiconductor and a conductor, on the substrate, and forcibly diffusing part of this film, e.g., by selective irradiation with high-energy ions, to form this part into an alloy semi-conductor, thereby providing a two-dimensional pattern of the fine lines of the conductor and the semiconductor. By arranging a plurality of fine lines of a conductor transversely to a direction of growth of a crack in the substrate, crack in the substrate is detected through a change in electrical resistance of the fine lines. A dissolved oxygen sensor, a hydrogen sensor, and an electrical conductivity sensor (of an ambient medium) can also be provided. To control water chemistry of a reactor, an amount of a water chemistry improving agent injected is controlled in accordance with an output of a water chemistry measurement sensor provided in water in a pressure vessel of the reactor. One or more of a dissolved oxygen sensor, a hydrogen sensor and an electrical conductivity sensor are formed directly on a surface of a structural material of the reactor.

20 Claims, 9 Drawing Sheets

SENSOR FOR CONTROLLING WATER QUALITY OF REACTOR AND METHOD OF CONTROLLING SAID WATER CHEMISTRY

BACKGROUND OF THE INVENTION

This invention relates to the art of controlling a water chemistry of nuclear reactor water, and more particularly to a sensor suitable for measuring the water chemistry of the reactor water as well as to a method of controlling the water chemistry of the reactor by the use of such a sensor.

It is thought that intergranular stress corrosion cracking (hereinafter referred to as "stress corrosion") of a structural material of a reactor occurs when three factors, that is, the composition and the stress of the material and the water chemistry, are all in undesirable conditions. Conventionally, in order that the reactor can be operated sufficiently safely from the viewpoint of stress corrosion, the carbon content of the structural material (particularly, stainless steel (SUS304)) of the reactor has been lowered, or a heat treatment has been applied to the structural material to relieve a residual stress. Thus, the conventional measures have coped with two (i.e., the material and the stress) of the three factors in the stress corrosion. Recently, in a boiling water-type reactor (BWR), hydrogen injection has been attempted in order to reduce dissolved oxygen in reactor water to improve the water chemistry (i.e., the third factor), as disclosed in Japanese Patent Unexamined Publication No. 57-3086.

In this prior art, a feed-water system, disposed downstream of a condenser of a primary cooling system of the BWR, is provided with a hydrogen injection device which is disposed upstream of a feed-water pump, and hydrogen injected from this hydrogen injector device is recombined with oxygen produced as a result of radiolysis of the water at a reactor core, in order to reduce the dissolved oxygen concentration in the various parts of the primary cooling system including a recirculation system.

A major part of the injected hydrogen shifts to a vapor phase under a boiling two-phase flow condition of the reactor core, and is discharged or emitted to the outside of the primary cooling system via a main steam piping and a turbine. When hydrogen is injected, hydrogen becomes greatly excessive relative to the oxygen being discharged simultaneously, and therefore it is necessary that upstream of the offgas oxygen-hydrogen recombiner, oxygen or the air of such an amount as corresponding to the excess of hydrogen should be supplied. In many cases, the oxygen concentration in the reactor water is measured usually by providing a sampling system in a reactor purification system.

It has been confirmed that stainless steel (SUS304), intentionally increased in sensitivity to corrosion, will not be subjected to stress corrosion if the dissolved oxygen is reduced to about 20 ppb.

Outside a pressure vessel, the effects of the hydrogen injection can be confirmed by measuring the dissolved oxygen concentration, using a water chemistry measuring system; however, there is no effective means for confirming the environment within the pressure vessel. Confirming means now used on a trial basis include sampling the water by the use of a neutron instrument pipe, and inserting a crack growth monitor into an instrument pipe so as to monitor the environment within the reactor core indirectly through the crack growth rate of a test piece made, for example, of stainless steel (SUS304). These measures have the following disadvantages:

(1) Since the sampling water, while flowing through the neutron instrument pipe, is reacted and recombined in accordance with the intensity of radiation exposure in the reactor, the measured value obtained outside the reactor does not represent the true environment within the reactor.

(2) In the crack growth evaluation device, electric current is applied from an external power source to both ends of a crack growth test piece as prestressed, and an electric potential between two specific points of the test piece is measured to determine the length of the crack. In order to ensure the precision of the measurement, it is necessary to use two pairs of potential-measuring points. Therefore, a total of six wires per test piece must be led in from the exterior of the reactor, and the number of test pieces is substantially limited to one for each neutron instrument pipe.

Therefore, in order to improve the evaluation precision, a plurality of sensors are needed. Further, other materials (e.g. inconel) than stainless steel (SUS304) are used as the structural material of the pressure vessel, for which evaluation is also required. And besides, a complicated software depending on a computer is needed for the evaluation of the crack growth behavior.

The hydrogen injection has another limitation. Namely, radioactive nitrogen (N-16) usually dissolved in the water in the form of nitric acid is reduced by the injected hydrogen into gas, so that the dose rate of the turbine system and hence that of the site boundary increase. In an example of the actual installation, it has been reported that the dose rate increased to about five times at the maximum with increase of the amount of the injected hydrogen. There is a tendency that the dose rate is kept constant below a certain threshold value of the hydrogen concentration, and abruptly increases above such a threshold value. Therefore, the amount of the hydrogen has an upper limit, and with respect to the hydrogen injection operation in the BWR, it is necessary to relieve the environment by injecting the hydrogen of an amount less than the upper limit.

Japanese Patent Application Nos. 62-259711 and 63-154767 describe that a radiation dose rate in the primary steam system can be reduced by injecting nitrous acid or nitric oxide gas. With such method, basically, the dissolved oxygen concentration can be reduced without increasing the radioactive nitrogen concentration in the turbine system. If the injected amount is excessive, the dissolved oxygen concentration increases although the radioactive nitrogen concentration decreases, and also the electric conductivity of the water becomes high, and a profile is formed in the primary system, which results in difficulty of the control.

SUMMARY OF THE INVENTION

It is an object of this invention to provide a method in which there is used as sensing element or sensor for determining and monitoring the optimum operating conditions for the injection of hydrogen and nitric oxygen gas to relieve a corrosion environment, without increasing a dose rate of a turbine system, so as to achieve the optimum operating conditions on the basis of such monitored values.

The present invention is directed to a sensing element usable within a pressure vessel of a reactor, a dissolved oxygen sensor utilizing such sensing element, a crack growth monitor utilizing such sensing element, and a sensor (utilizing such sensing element) for measuring electrical conductivity of high-temperature water, and a method and system for operating a boiling water-type reactor, using such sensors.

The points where hydrogen and nitrous acid are injected are usually at the feed-water system; however, the nitrous acid is not injected directly so as not to increase an electrical conductivity of the feed water, but is injected in the form of nitric oxide gas to be reacted with a product of decomposition of the water, thereby ensuring a required nitrous acid concentration at an inlet of a reactor core. This method is practical. In this case, the electrical conductivity of the water varies in a primary cooling system in accordance with the degree of conversion of the nitric oxide gas into the nitrous acid.

Therefore, in order to achieve the above object, the following operating conditions are necessary:

(1) The amounts of hydrogen and nitric oxide gas as injected are so controlled that radioactive nitrogen will not exceed a level obtained in the normal operating condition.

(2) The nitrous acid concentration is controlled to a predetermined level at the reactor core inlet.

(3) The amount of nitric oxide gas as injected is so controlled that the oxygen concentration in the vicinity of the reactor core will not exceed a predetermined level.

(4) In order to indirectly monitor complex corrosion environment relief effects (due to oxygen, nitrous acid and etc.) within the reactor pressure vessel, a plurality of crack growth monitors are provided within the pressure vessel.

To realize this operating method, there are needed a radioactive nitrogen monitor in a main steam line, a nitrous acid concentration monitor in the vicinity of the reactor core inlet, a dissolved oxygen monitor within the pressure vessel, and a plurality of crack growth monitors within the pressure vessel. Among these, the radioactive nitrogen monitor is conventionally available, but the nitrous acid concentration monitor in the vicinity of the reactor core inlet and the dissolved oxygen monitor within the pressure vessel have not existed heretofore, and the conventional crack growth monitor can not always be used efficiently, as described above.

The inventor of the present invention has invented an element applicable to these monitors which element has a plurality of thin film conductor lines formed on a semi-conductor or an insulator. By measuring electrical resistance of the fine line or electrical resistance between the fine lines, the dissolved oxygen concentration in the reactor water, the electrical conductivity and the crack growth rate can be monitored, as described later.

According to a first invention, there is provided an element comprising a non-electrically conductive substrate, and a fine-line forming thin film of a conductor formed on a surface of the substrate such that a change in physical properties of one of the substrate and the ambient environment is detected through a change in physical properties of the conductor.

According to a second invention, there is provided a method of manufacturing an element, comprising the steps of forming a layered film, composed of a semi-conductor and a conductor, on a surface of a substrate; and forcibly diffusing a part of the film so as to change the part into an alloy semi-conductor, thereby forming a two-dimensional pattern composed of fine lines of the conductor and the semi-conductor.

According to a third invention, there is provided a method of manufacturing an element, comprising the steps of forming a layered film, composed of a semi-conductor and a conductor, on a surface of a substrate; and irradiating high-energy ions to a part of the film to forcibly diffuse the part of the film so as to change the part into an alloy semi-conductor, thereby forming a two-dimensional pattern composed of the conductor and the semi-conductor.

According to a fourth invention, there is provided a sensor comprising a substrate; a thin film made of a semi-conductor or an insulator and formed on the substrate; and a plurality of fine lines of a conductor formed on the thin film such that deformation of the substrate is detected through a change in resistance of the fine lines.

According to a fifth invention, there is provided a sensor comprising a substrate; a thin film made of a semi-conductor or an insulator and formed on said substrate; a plurality of fine-line forming thin films formed on the thin film in such a manner that the fine-line forming thin films extend transversely to a direction of growth of a crack in the substrate, the crack in the substrate being detected through a change in resistance of the fine-line forming thin films.

According to a sixth invention, there is provided a dissolved oxygen sensor comprising an oxygen-permeable substrate; a fine-line forming thin film pattern formed on the substrate; and a coating of a semi-conductor or an insulator covering the fine line forming thin film pattern such that an ambient oxygen concentration is detected through a value of an electrical resistance of fine lines of the thin film.

According to a seventh invention, there is provided a hydrogen sensor comprising a substrate; a thin film made of a semi-conductor or an insulator and formed on the substrate; and a fine-line forming thin film formed on the thin film and made of metal capable of occluding hydrogen such that an ambient hydrogen concentration is detected by a value of an electric resistance of the fine lines of the fine-line forming thin film.

According to an eighth invention, there is provided an electrical conductivity sensor comprising at least three fine-line forming thin films of a conductor formed on a semi-conductor or an insulator and spaced from one another at different intervals such that an electrical conductivity of the ambient medium is detected through a difference in electrical resistance value between adjacent ones of the fine-line forming thin films.

According to a ninth invention, there is provided a reactor comprising a water chemistry measurement sensor provided in water in a pressure vessel of the reactor.

According to a tenth invention, there is provided a method of controlling a water chemistry in a reactor, comprising the step of controlling an amount of a water chemistry improving agent being poured in accordance with an output of a water chemistry measurement sensor provided in water in a pressure vessel of the reactor.

According to an eleventh invention, there is provided a reactor comprising one or more of the above dissolved oxygen sensor (the sixth invention), the above hydrogen sensor (the seventh invention) and the above electrical conductivity sensor (the eighth invention), any of these sensors being formed directly on a structural material of the reactor.

DESCRIPTION OF THE PREFERRED EMBODIMENTS

Figure 2:
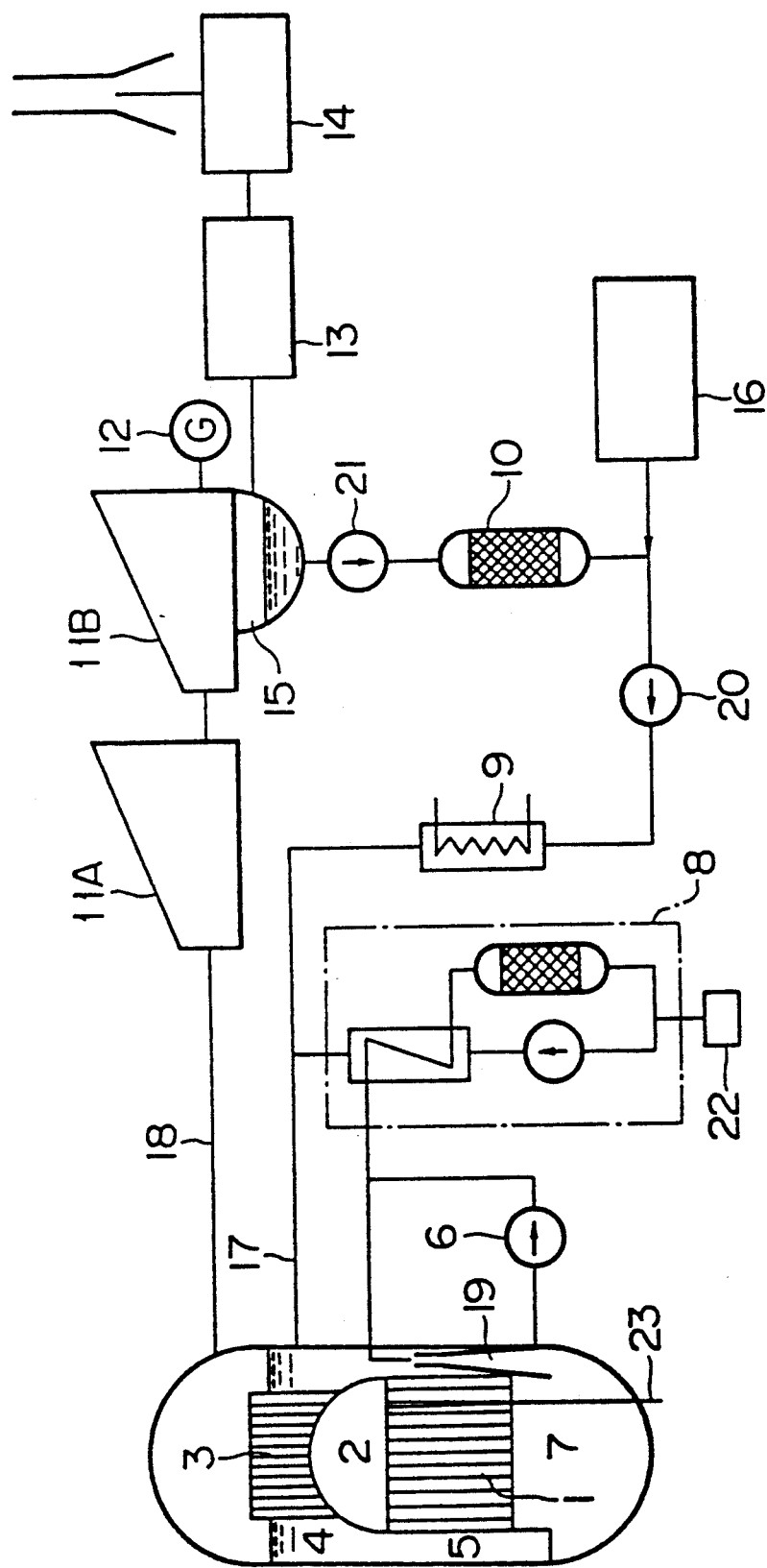
FIG. 2 is a diagram of a primary cooling system of a reactor.

FIG. 2 shows main lines or circuits of a primary cooling system of a boiling water-type reactor (BWR). In FIG. 2, reference numeral 1 denotes a reactor core, 2 an upper plenum, 3 a steam separator, 4 a mixing plenum, 5 a downcomer, 6 a recirculation pump, 7 a lower plenum, 8 a reactor purification system, 9 a feed-water heater, 10 a condensate demineralizer, 11A a high-pressure turbine, 11B a low-pressure turbine, 12 a generator operated by these turbines, 13 a oxygen-hydrogen recombiner, 14 a noble gas hold-up, 15 a condenser, 16 a hydrogen injection device, 17 a feed-water piping, 18 a main steam piping, 19 a jet pump, 20 a feed-water pump, and 21 a condenser pump. The feed-water system disposed downstream of the condenser 15 is provided with the hydrogen injection device 16 upstream of the feed-water pump 20. Hydrogen injected from the device 16 is recombined with oxygen, which is produced by radiolysis of water at the reactor core 1, to reduce a dissolved oxygen concentration in the primary cooling system. A major part of the injected hydrogen is transferred to a vapor phase under a boiling two-phase flow condition of the reactor core 1, and is discharged or emitted to the outside of the primary cooling system via the main steam piping 18 and the turbines 11. When injected, hydrogen becomes greatly excessive relative to the oxygen being discharged simultaneously, and therefore it is necessary that upstream of the oxygen-hydrogen recombiner 13, oxygen or the air of such an amount as corresponding to the excess of hydrogen should be supplied. The oxygen concentration of the reactor water is measured usually by providing a sampling system in the reactor purification system 8.

Figure 3:
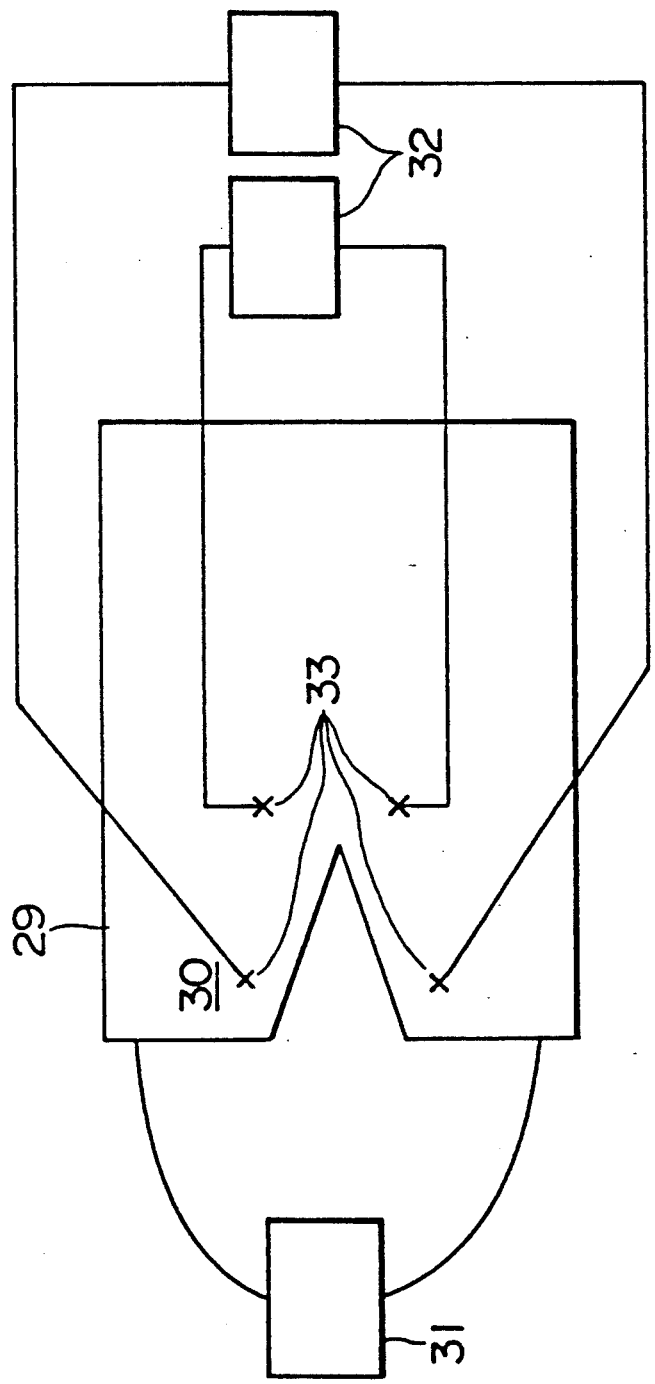
FIG. 3 is a schematic view of a conventional crack growth monitor.

FIG. 3 schematically shows a conventional crack growth evaluation device. Electric current is applied from an external power source 31 to both ends of a crack growth test piece 29 as prestressed, and an electric potential between each of two pairs of points 30, 33 of the test piece 29 is measured by measuring devices 32 to determine the length of the crack. A total of six lead wires are led to the crack test piece 29 (disposed within the reactor) through a neutron instrument pipe from the power source 31 and measuring devices 32 disposed outside of the reactor.

Figure 4:
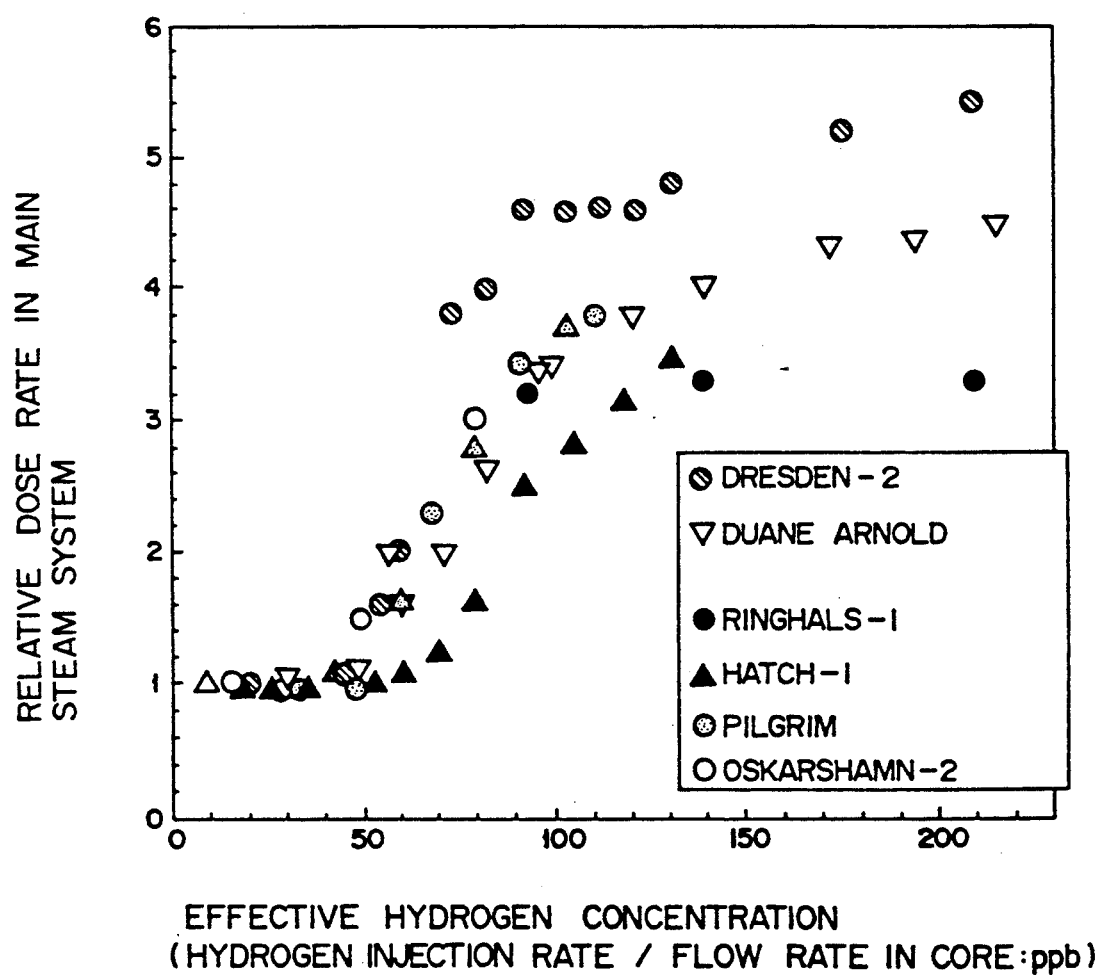
FIG. 4 is a graph representing variations in dose rate of a turbine system when injecting hydrogen into a reactor.

FIG. 4 shows variations in a dose rate relative to the hydrogen concentration in an actual installation, and it will be appreciated that the dose rate is substantially constant below a predetermined threshold value of the hydrogen concentration, and abruptly increases above the threshold value of the hydrogen concentration.

Figure 5:
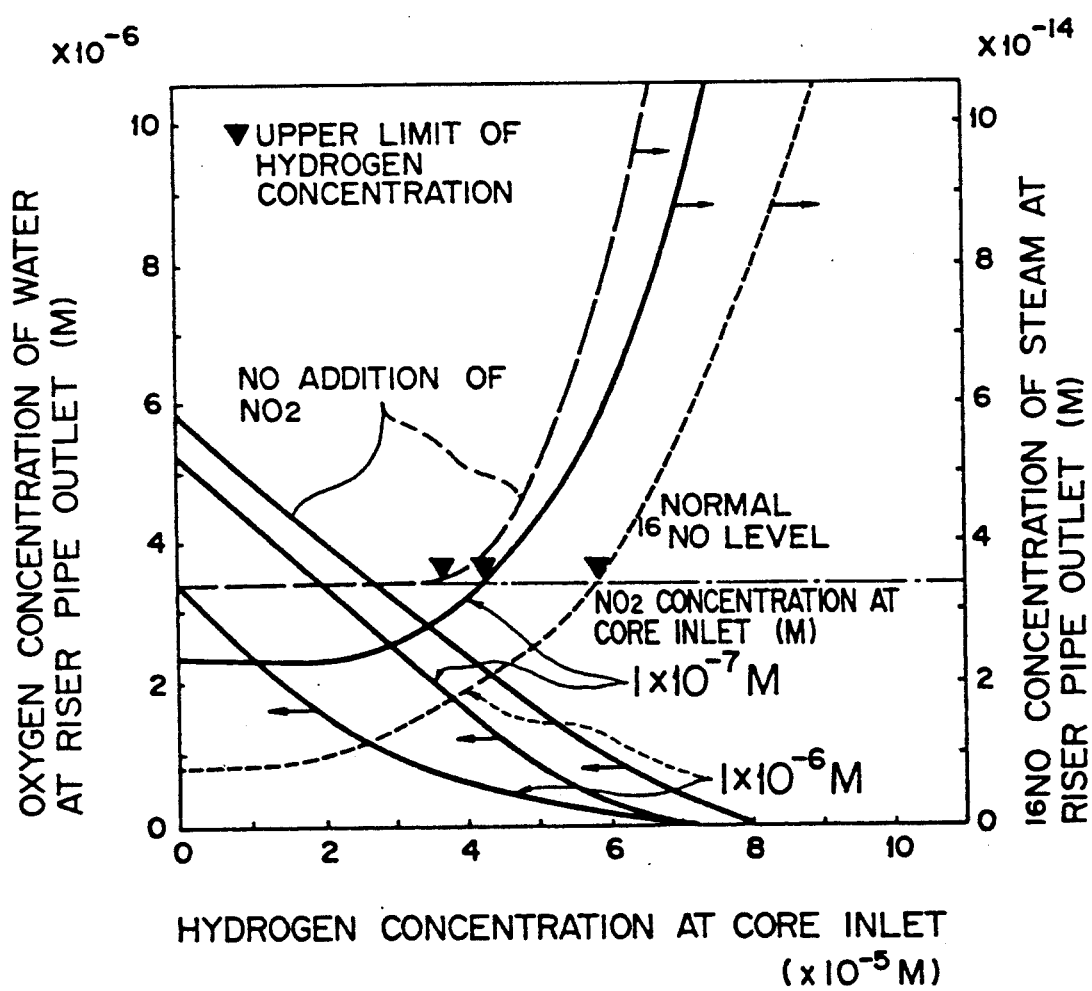
FIG. 5 is a graph representing calculation values of an oxygen concentration in water at an riser pipe outlet and a radioactive nitrogen ($^{16}NO$) concentration in steam at the riser pipe outlet when adding hydrogen and nitrous acid.

FIG. 5 shows an oxygen concentration of the water and a radioactive nitrogen concentration of the main steam at an outlet of a riser pipe relative to a hydrogen concentration at a reactor core inlet. Nitric oxygen gas is injected, and reacts with the product of decomposition of the water to be converted into nitrous acid. It will be appreciated that when the nitrous acid is added together with the hydrogen, the concentration of the radioactive nitrogen $^{16}N$ decreases as compared with the case where the nitrous acid is not added, and that the oxygen concentration further decreases in the range of this nitrous acid concentration.

Figure 6:
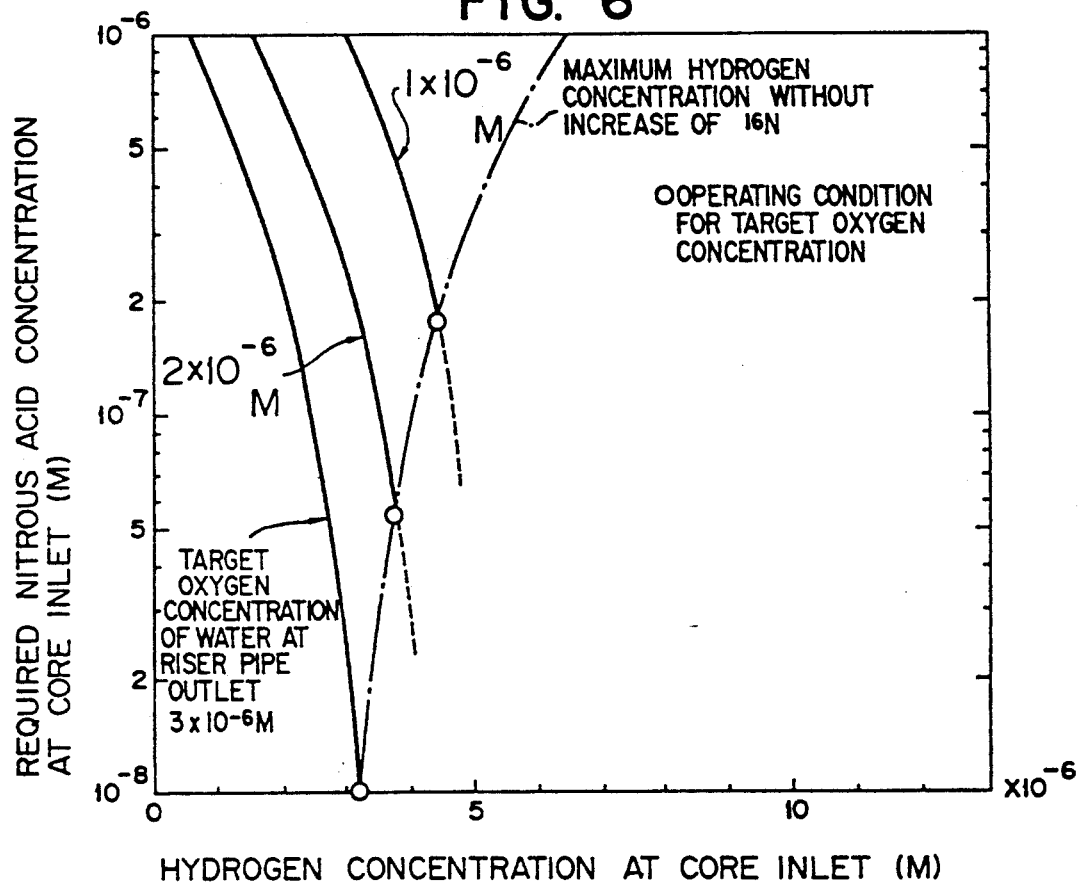
FIG. 6 is a graph showing the relation between the hydrogen concentration and the nitrous acid concentration at a reactor core inlet, which is required to achieve a specific oxygen concentration in the water at the riser pipe outlet.

FIG. 6 shows a combination of the hydrogen concentration and the nitrous acid concentration at the reactor core inlet relative to the target oxygen concentration at a reactor core outlet. FIG. 6 also shows such an upper limit of the amount of the injected hydrogen as not to increase the radioactive nitrogen.

Figure 7:
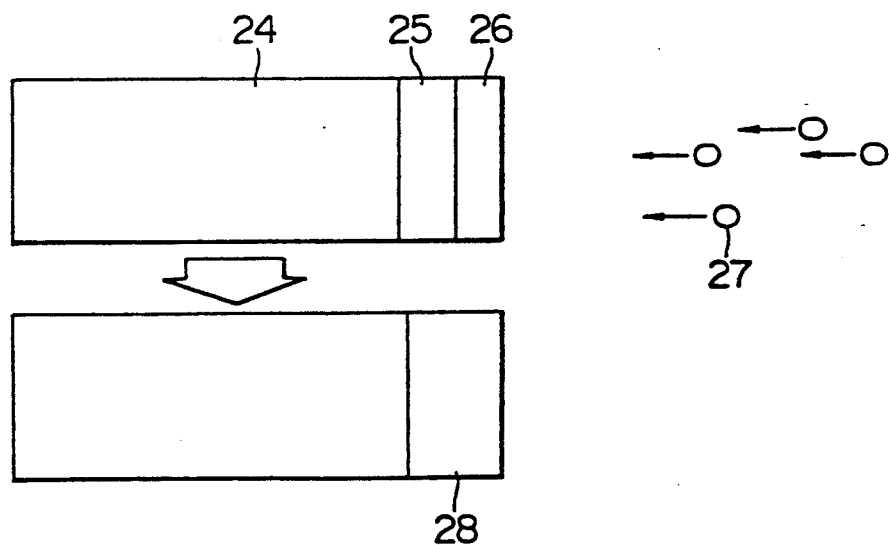
FIG. 7 is a schematic view illustrative of an ion mixing.
Figure 8:
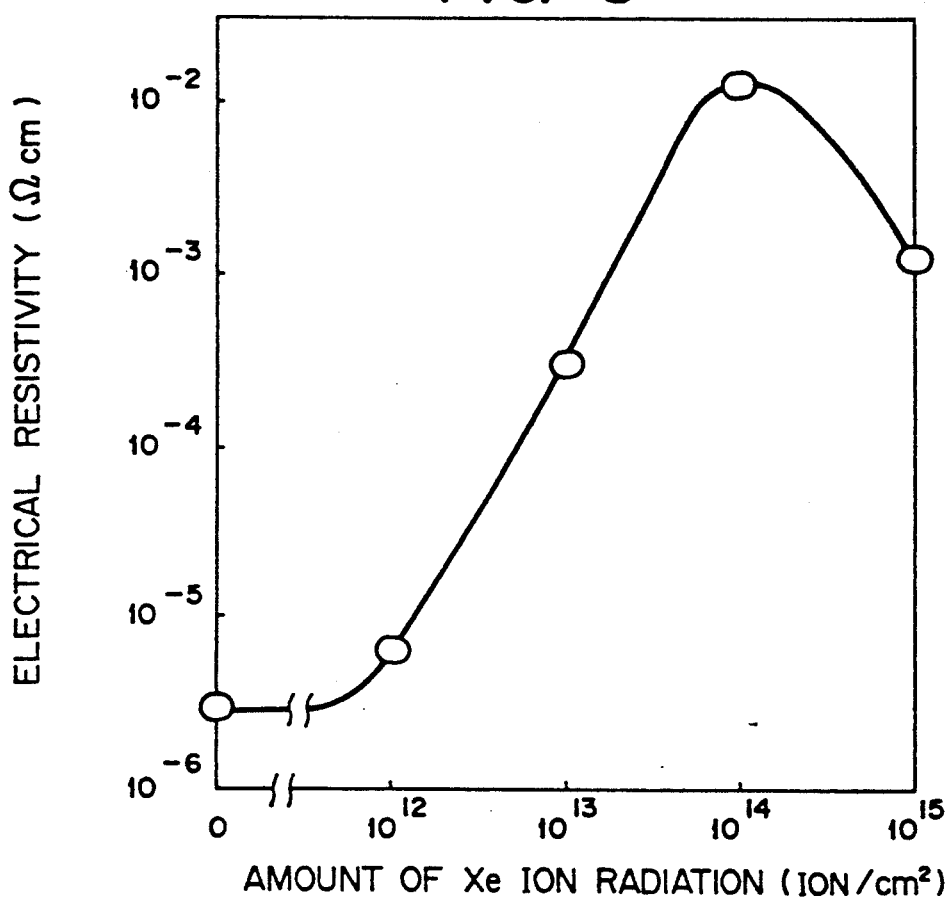
FIG. 8 is a graph representing variations in electrical resistance of a compound of ruthenium and silicon upon irradiation of ions.

The inventor of the present invention has discovered a phenomenon suitable for forming a fine-line forming thin film. As shown in FIG. 7, a multi-layer film composed of a silicon (Si) layer 25 and a ruthenium (Ru) layer 2 is formed on a specific substrate 24, and for example, ions 27 of high energy are irradiated to this multi-layer film to effect a forcible mixing (ion mixing) of ruthenium and silicon. As shown in FIG. 8, the resulting compound 28 of ruthenium and silicon involving a lattice defect is higher by several orders in electrical resistance than the multi-layer film which is not subjected to irradiation of ions. Therefore, by forming a mask on the multi-layer film of FIG. 7 with a photoresist or the like, and then by irradiating high-energy ions to those portions other than the fine-line-forming portions, the irradiated portions increases in electrical resistance whereas the non-irradiated portions can ensure electric conductivity thanks to the ruthenium.

Figure 1:
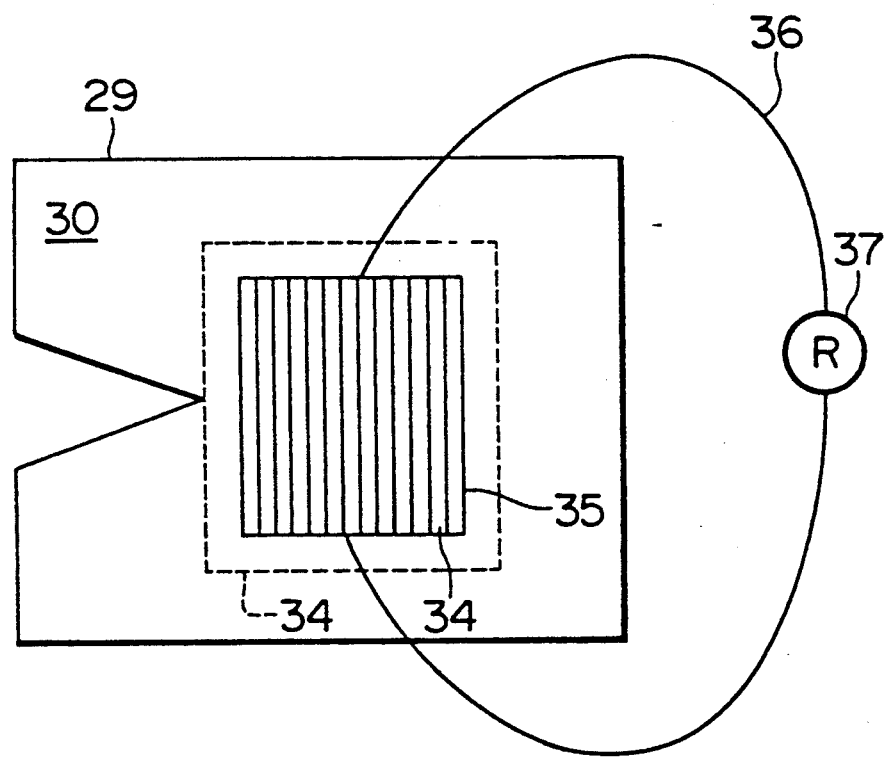
FIG. 1 is a schematic view of one preferred embodiment of a crack growth monitor of the present invention.

FIG. 1 shows a material crack growth monitor prepared by application of the principle of the present invention. A pattern comprising a thin film 34 which is made of either an electrical insulator having a sufficiently high electrical resistance at service condition temperatures or a semi-conductor and fine-line forming thin film 35 of a conductor is formed on one or both sides or faces 30 of a crack test piece 29 used for a crack growth rate measurement. An electrical resistance between opposite end points of this pattern is measured by a resistance measuring device 37, and the fine-line forming thin film 35 of a conductor are cut as the cracking of the crack test piece 39 proceeds, so that the overall electrical resistance of the fine-line pattern increases. The overall resistance of the fine-line pattern is proportional to the length of the crack in a ratio of 1:1, and therefore the length of the crack can be determined by measuring this electrical resistance.

A suitable example of material for the thin film 34 is a semi-conductor such as the above-mentioned silicon and germanium, and suitable examples of material for the fine-line forming film 35 are the above-mentioned ruthenium, iron and chromium. One method of forming the pattern will now be described with reference to FIG. 1. First, in order to electrically insulate the crack test piece 29 from the conductive fine-line forming thin film 35 of the pattern, the thin film 34 of an insulator or a semi-conductor is formed on one side of the crack test piece 29. Vapor deposition and sputtering are suitable for this formation. If the bonding or adhering of the thin film 34 to the test piece material is poor, a film having a thickness generally corresponding to the flight range of the high-energy ions is beforehand formed, and then the high-energy ions are irradiated to this film to forcibly mix the crack test piece 29 and the thin film 34 together, thereby improving the bonding. If necessary, a thin film of a semi-conductor or an insulator is further formed on the thus formed thin film 34 so as to make the thin film 34 thick to a predetermined thickness. The thin film 35 which will mix with the substrate to form a semi-conductor or an insulator is formed on the thin film 34.

Figure 9:
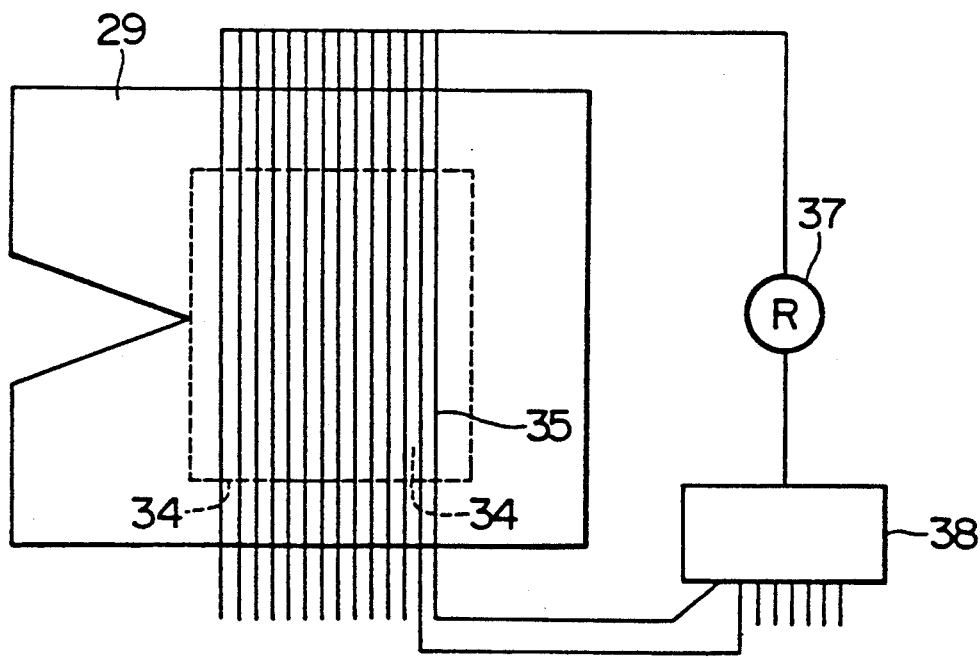
FIGS. 9 and 10 are views of modified crack growth monitors of the invention, respectively.
Figure 10:
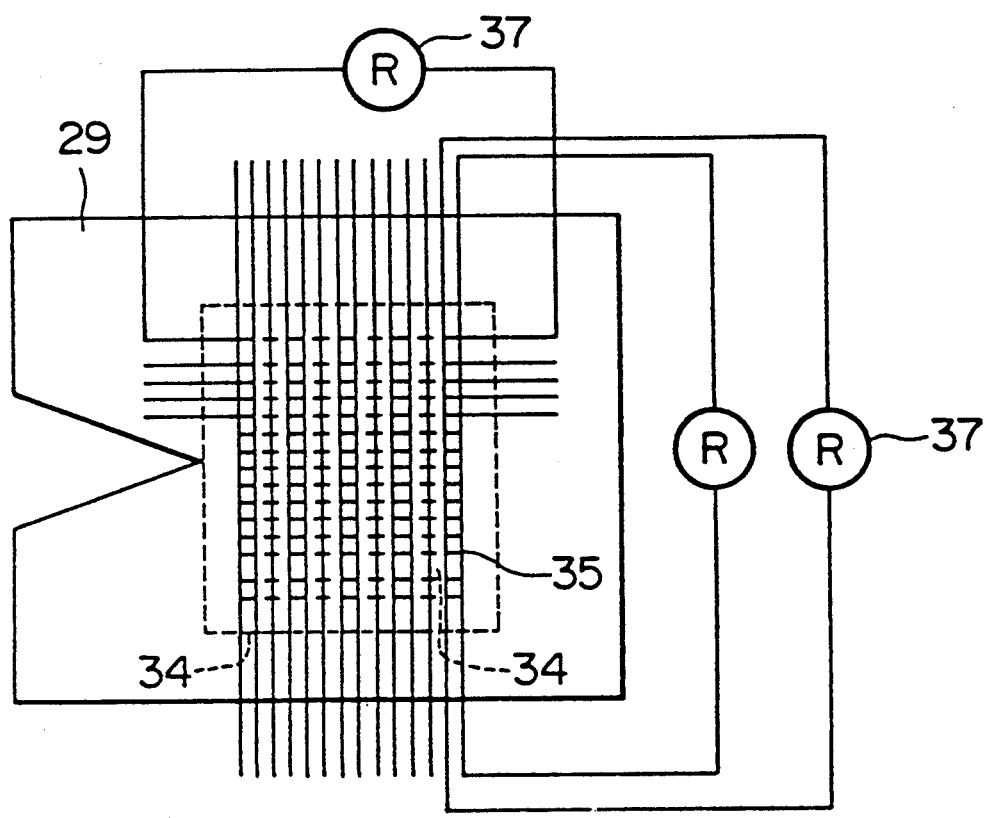

When the material for the semi-conductor thin film 34 is silicon, a suitable material for the fine-line forming thin film 35 is ruthenium, iron or chromium. Then, in order to provide a predetermined pattern, a mask is formed on the thin film on the thin film by a photoresist or the like, and then high-energy ions are irradiated to the thin film. As described above with reference to FIGS. 7 and 8, the non-masked area of the thin film undergoes a forcible mixing by irradiation of ions to form a semi-conductor, for example, of a ruthenium-silicon compound. On the other hand, the masked area of the thin film remains as the conductor, so that the intended thin-line pattern composed of the conductor and the semi-conductor is formed on the one side of the crack test piece 29. Lead wires 36 such as gold wires for measuring the resistance are connected in position by spot welding. The growth of the crack can also be monitored by separately measuring the resistances of the fine lines as shown in FIG. 1 by means of a multiplexer 38 as shown in FIG. 9. Particularly where the pattern of FIG. 9 is modified in such a manner that the lines of the pattern are in a two-layer form with the upper-layer lines intersecting the lower-layer lines as shown in FIG. 10 or where the pattern lines on one side of the crack test piece 29 are so disposed as to intersect the pattern liens on the other side, the two-dimensional position of the distal end of the crack can be detected. When the environment around the crack test is of an oxidizing nature, the conductor portions are oxidized, so that their resistances are changed. Measurement errors due to this can be eliminated by further forming a film of a semi-conductor (e.g. silicon) or an insulator on the surface of the element. The resistance change due to such oxidation can be used in a sensor for measurement of an oxygen concentration of the environment.

Figure 11:
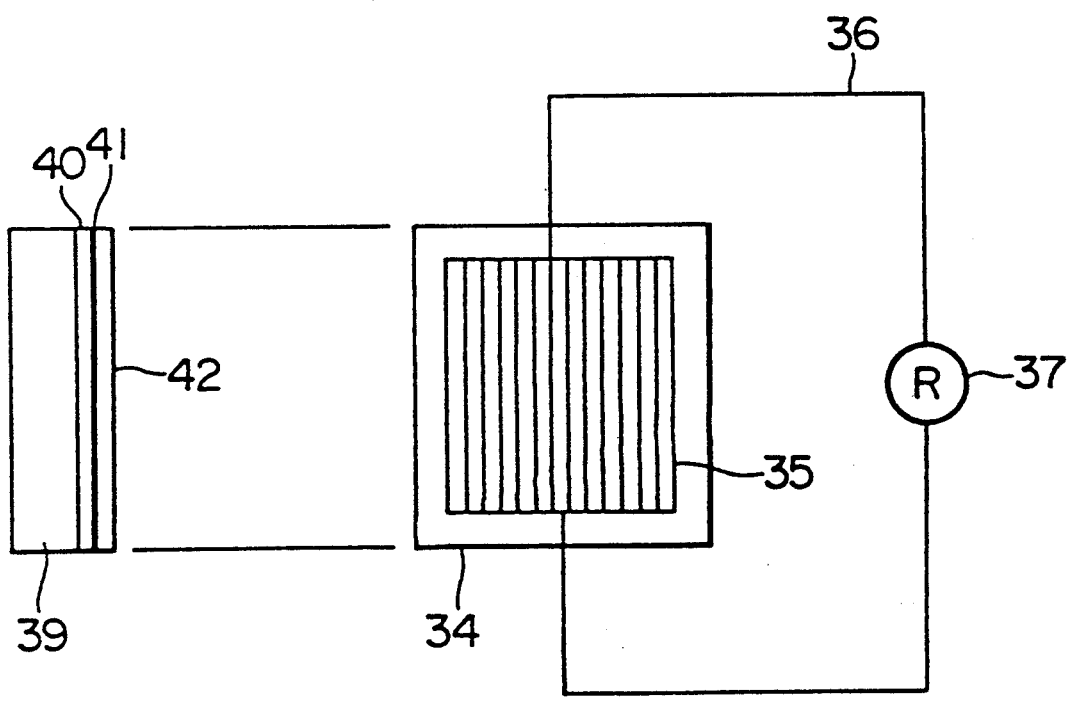
FIG. 11 is a schematic view of a dissolved oxygen sensor according to another embodiment of the invention.

FIG. 11 shows the construction of such an oxygen sensor. A film 40 of metal such as iron susceptible to oxidation is first vapor-deposited on a ceramics 39 such as zirconium oxide for which oxygen is permeable. Then, a film 41 of a semiconductor such as silicon is vapor-deposited on the metal film 40 to the extent that the sum of thicknesses of the metal film 40 and the semi-conductor film 41 generally correspond to the flight range of ions being irradiated. Then, the high-energy ions are irradiated to locally produce an alloy semi-conductor (FeSi), thereby forming a fine-line pattern of iron. If oxygen permeating through the semi-conductor film 41 is obstructive, a film having a low oxygen-permeability may be added. Such a film as additionally vapor-deposited may be made of metal if it is sufficiently insulated from the iron film.

Figure 12:
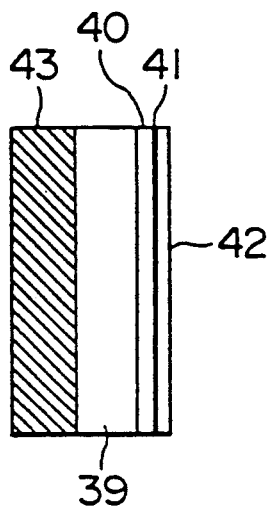
FIG. 12 is a view of a modified dissolved oxygen sensor according to another embodiment of the invention.

FIG. 12 shows an oxygen sensor for sensing dissolved oxygen in the primary cooling water in the reactor. In order to prevent the oxidation of fine lines before the operation of the reactor, a protective film 43 is formed on a substrate 39 of zirconium. The protective film 43 is made of a material for example, Teflon which dissolves in high-temperature water to disappear. A dynamic range of the measurement can be increased by adjusting the thickness of the conductor film 40 or the thickness of the zirconium oxide film 39.

Figure 13:
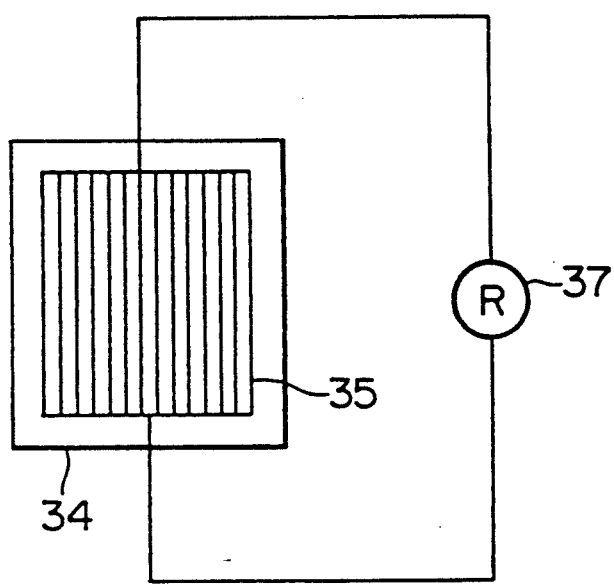
FIG. 13 is a schematic view of a hydrogen sensor according to an embodiment of the invention.

The same principle can be applied to a hydrogen sensor as shown in FIG. 13. In this case, as a conductor component 40 (see FIG. 12), metal capable of occluding hydrogen, such as palladium and titanium, is selected. The hydrogen concentration in the environment can be measured on the basis of a change of the resistance corresponding to the amount of hydrogen as occluded.

Figure 14:
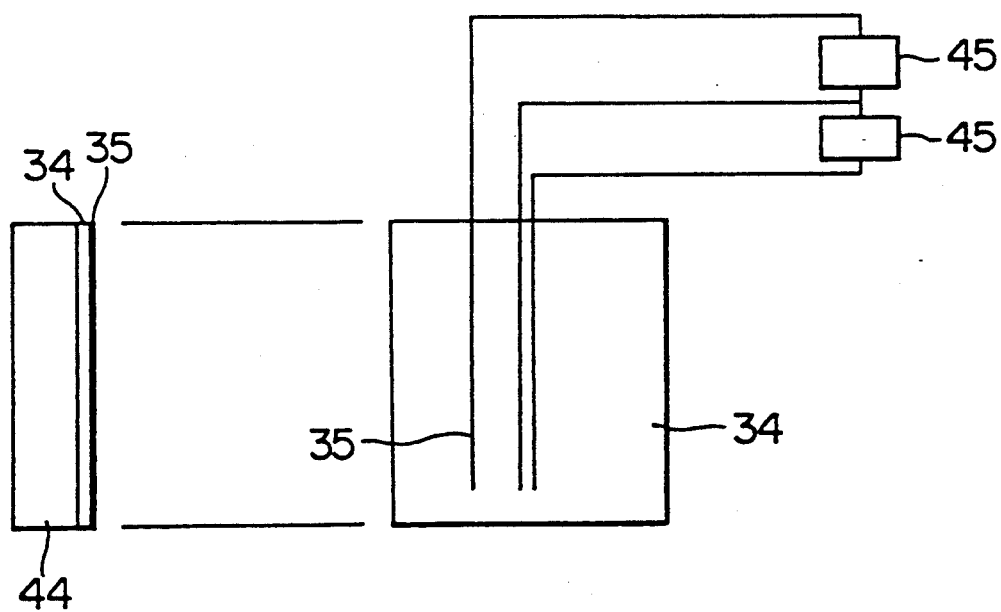
FIG. 14 is a water electrical conductivity sensor according to the invention.

As shown in FIG. 14, an element having a plurality of fine-line forming thin films 35 is placed in water, and the conductivity of the water can be measured by measuring DC or AC resistances of two fine-line forming thin films.

Since the above-mentioned sensors are all composed of metal and a semi-conductor, and in some cases ceramics, they can be used in a high-temperature, high-pressure and high-radiation condition, as in the pressure vessel of the reactor.

Therefore, a water chemistry control method (as shown in FIGS. 5 and 6) utilizing such sensors will now be described.

FIG. 5 shows the relationship of the hydrogen concentration at the reactor core inlet, the oxygen concentration of the water at the riser pipe outlet, and the $^{16}NO$ concentration of the steam at the riser pipe outlet, which relationship depends on the nitrous acid concentration at the reactor core inlet. While circulated in the reactor primary system, the injected components are subjected to radiation to be changed in their chemical forms, and are accumulated in the water during the circulation, and therefore there has heretofore existed no means for knowing the nitrous acid concentration at the reactor core inlet. However, by positioning the sensor of FIG. 14 in the vicinity of the lower plenum or the lower grid within the pressure vessel of the reactor, the nitrous acid concentration can be detected indirectly on the basis of the conductivity at that position, so that the amount of nitrogen oxides being injected can be controlled.

Among the structural parts or materials for the reactor, the primary system, piping, a pressure boundary such as a pressure vessel, and a lower grid for supporting the weight of the reactor are important. The oxygen sensors shown in FIGS. 11 and 12 are small-sized, and therefore can be relatively readily mounted at any position in the primary system.

For example, if the oxygen sensor is mounted on a lower portion of the pressure vessel through a neutron instrument pipe, the true water chemistry in the lower structure of the reactor can be known, and by determining the amount of hydrogen being detected in accordance with its monitored value, a highly-reliable water chemistry control can be effected.

The oxygen sensor and the conductivity sensor are both mounted at the lower portion of the reactor core, and the amounts of hydrogen and nitric oxide being injected are so controlled as to satisfy the relation shown in FIG. 6, so that the water quality can be controlled without increasing the dose rate of the turbine system.

Further, by affixing the oxygen sensor to the surface of a selected structural material of the reactor or forming the oxygen sensor directly on the surface, the oxygen concentration at a desired position near any structural material within the reactor can be known, thus improving the reliability of the water chemistry control.

Such sensor can be used for off-line measurement. More specifically, lead wires are not led out from the pressure vessel during the operation of the reactor, but sensors are formed on the surface of the structural material, and a change in resistance is measured at the time of periodic inspection of the reactor, so that there can be known the average oxygen concentration in the water in which the material having the sensors formed thereon is placed.

As described above, according to the present invention, there are provided a crack growth monitor, a dissolved oxygen sensor and a conductivity sensor which can be used in severe environments of a reactor primary system and which are used to measure a dissolved oxygen concentration, a dissolved hydrogen concentration and a nitrous acid concentration in the reactor water. By using their outputs, the amounts of additive hydrogen, nitrous acid, etc., are controlled, thereby securing the soundness of the material of the reactor, which is very advantageous from the viewpoints of safety and the securing of the energy source.

What is claimed is:

1. An element comprising a non-electrically conductive member and at least one fine-line thin film of a conductor adjacent a surface of said member such that a change in physical properties of one of said member and ambient environment is detected through a change in physical properties of said conductor, with a mixture of material of the conductor and material of the non-electrically conductive member provided at sides of the at least one fine-line thin film of the conductor.

2. An element according to claim 1, in which a plurality of said fine-line thin films of the conductor are provided adjacent the surface of said member such that a change in physical properties of one of said member and the ambient environment is detected through a physical property change between fine lines of said fine-line thin films.

3. An element according to claim 1, in which a plurality of said fine-line thin films of a conductor are provided adjacent the surface of said member, said fine-line thin films being made of a metal capable of occluding hydrogen, and wherein said mixture is provided between any adjacent ones of said fine-line thin films to form mixture thin films, such that a change in physical properties of said mixture thin films is detected as a physical property change between said fine lines, and a change in physical properties of one of said member and the ambient environment is detected through said physical property change between said fine lines.

4. An element according to claim 3, in which one or more of said fine-line thin films, as well as one or more of mixture thin films, are formed on the surface of said member such that a change in physical properties of one of said member and the ambient environment is detected through a physical property change between said mixture thin films and said fine lines.

5. An element according to claim 4, wherein said metal capable of occluding hydrogen is selected from the group consisting of palladium and titanium.

6. An element according to claim 1, wherein said mixture of material of the conductor and material of the non-electrically conductive member is a compound of the material of the conductor and the material of the non-electrically conductive member.

7. An element according to claim 1, wherein said mixture of material of the conductor and material of the non-electrically conductive member is an alloy of the material of the conductor and the material of the non-electrically conductive member.

8. An element according to claim 1, wherein the material of the non-electrically conductive member is selected from the group consisting of silicon and germanium.

9. An element according to claim 8, wherein the material of the conductor is selected from the group consisting of ruthenium, iron and chromium.

10. An element according to claim 1, further comprising a further film of a non-electrically conductive material adjacent a surface of the at least one fine-line thin film opposite the surface of the thin film adjacent said member.

11. An element according to claim 1, wherein the non-electrically conductive member is a substrate, the at least one fine-line thin film being provide on the substrate.

12. An element according to claim 11, wherein said substrate includes a layer of material of the non-electrically conductive member on a sub-member.

13. An element according to claim 1, wherein the at least one fine-line thin film is provided on a substrate, the non-electrically conductive member being provided on the at least one fine-line thin film.

14. An element according to claim 13, wherein the substrate is formed of an oxygen permeable material.

15. A sensor comprising a substrate; a thin film made of a semi-conductor or an insulator and formed on said substrate; and a plurality of fine lines of a conductor formed on said thin film such that deformation of said substrate is detected through a change in resistance of said fine lines, with a mixture of material of the thin film and material of the fine lines provided between adjacent fine lines.

16. A sensor comprising a substrate; a thin film made of a semi-conductor or an insulator and formed on said substrate; a plurality of fine-line thin films of a conductor formed on said thin film in such a manner that said fine-line thin films extend transversely to a direction of growth of a crack in said substrate, said crack in said substrate being detected through a change in resistance of said fine-line thin films, with a mixture of material of the thin film and material of the fine-line thin films provided between adjacent fine-line thin films.

17. An element comprising a non-electrically conductive member and at least one fine-line thin film of a conductor provided adjacent said non-electrically conductive member, with a mixing of material of the non-electrically conductive member and material of the conductor at sides of the at least one fine-line thin film, said mixing being achieved by forcibly diffusing together material of the non-electrically conductive member and material of the conductor, such that a change in physical properties of one of said member and ambient environment is detected through a change in physical properties of said conductor.

18. A sensor comprising a substrate; a thin film made of a semiconductor or an insulator and formed on said substrate; a plurality of fine-line thin films of a conductor provided on said thin film in such a manner that said fine-line thin films extend transversely to a direction of growth of a crack in said substrate, said crack in said substrate being detected through a change in resistance of said fine-line thin films, the sensor further comprising further fine-line thin films of a conductor similar to said fine-line thin films, provided in superposed relation thereto in such a manner that upper and lower layers of fine lines extend in different directions, respectively, the position of the crack in said substrate being detected through values of electrical resistances of said upper and lower layers of said fine lines.

19. A sensor according to claim 18, wherein the upper and lower layers of fine-lines are provided on a same side of said substrate.

20. A sensor according to claim 18, wherein the upper and lower layers are provided on opposite sides of said substrate.

* * * * *